United States Patent [19]
Harvey, III et al.

[11] Patent Number: 5,945,832
[45] Date of Patent: Aug. 31, 1999

[54] STRUCTURE AND METHOD OF MEASURING ELECTRICAL CHARACTERISTICS OF A MOLECULE

[75] Inventors: Thomas B. Harvey, III, Scottsdale; Chan-Long Shieh, Paradise Valley, both of Ariz.

[73] Assignee: Motorola, Inc., Schaumburg, Ill.

[21] Appl. No.: 09/024,147

[22] Filed: Feb. 17, 1998

[51] Int. Cl.$^6$ .............................. G01N 27/07; G01R 27/08
[52] U.S. Cl. .......................... 324/693; 324/71.4; 324/724
[58] Field of Search .................................. 324/71.1, 71.4, 324/691, 693, 696, 713, 715, 717, 718, 722, 724; 361/271, 281

[56] References Cited

U.S. PATENT DOCUMENTS 3,995,216  11/1976  Yun ......................................... 324/678
5,457,396  10/1995  Mori et al. .............................. 324/71.4

*Primary Examiner*—Diep Do
*Attorney, Agent, or Firm*—Eugene A. Parsons; William E. Koch

[57] ABSTRACT

A method of measuring electrical characteristics of a molecule including providing a first metal contact having a major surface, an insulating layer overlying the major surface of the first metal contact and a second metal contact overlying the insulating layer so as to have an edge spaced a molecular distance from the major surface of the first metal contact. A conductive organic molecule including a metal binding group is coupled between the metal contacts.

18 Claims, 1 Drawing Sheet

STRUCTURE AND METHOD OF MEASURING ELECTRICAL CHARACTERISTICS OF A MOLECULE

FIELD OF THE INVENTION

The present invention relates to analyzing molecules, and more particularly to the use of electrical conduction to determine characteristics of a molecule.

BACKGROUND OF THE INVENTION

In the discipline of nano electronics, researchers are interested in the electrical properties of individual molecules. By measuring various electrical characteristics, much about different molecules can be determined. Determining the electrical properties of molecules requires the fabrication of electrodes separated by a gap of molecular dimensions such as approximately 10–100 angstroms. Currently ultra-fine gap electrodes are fabricated by forming thin metal lines on an insulating substrate. The substrate is then bent until the thin metal line fractures, producing a gap of molecular dimensions. The insulating substrate is typical bent using a piezoelectric actuator. The molecules to be tested are then bound by their ends to the metal line at opposing sides of the gap.

While this process achieves the desired results, namely producing an ultra-fine gap electrode structure, the process of fabrication of the structure is not highly reproducible due to the variables of fracturing the thin metal line. Furthermore, multiple structures cannot be simultaneously fabricated using this process.

It would be highly advantageous, therefore, to remedy the foregoing and other deficiencies inherent in the prior art.

Accordingly, it is an object of the present invention to provide a new and improved method of fabricating ultra-fine gap electrodes.

Another object of the present invention is to provide a method which permits the fabrication of multiple ultra-fine gap electrode structures simultaneously and more readily and consistently fabricating ultra-fine gap electrodes.

And another object of the present invention is to provide a method of fabricating ultra-fine gap electrodes employing semiconductor processing techniques.

SUMMARY OF THE INVENTION

Briefly, to achieve the desired objects of the instant invention in accordance with a preferred embodiment thereof, provided is a device for measuring electrical characteristics of a molecule. The device includes a first metal contact having a major surface, an insulating layer overlying the major surface of the first metal contact, and a second metal contact overlying the insulating layer and having an edge spaced a molecular distance from the major surface of the first metal contact.

Also to achieve the desired objects of the instant invention provided is a method for fabricating a device for measuring electrical characteristics of a molecule. The method includes providing a first metal contact having a major surface, forming an insulating layer overlying the major surface of the first metal contact, and positioning a second metal contact overlying the insulating layer so as to have an edge spaced a molecular distance from the major surface of the first metal contact.

And also to achieve the desired objects of the instant invention, provided is a method of fabricating a device for measuring electrical characteristics as described previously and further including electrically connecting a conductive organic molecule including a metal binding group at each end, between the first metal contact and the second metal contact. A measuring device is connected between the first and second metal contacts, and the electrical characteristics of the conductive organic molecule are measured.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DESCRIPTION OF THE PREFERRED EMBODIMENTS

Figure 1:
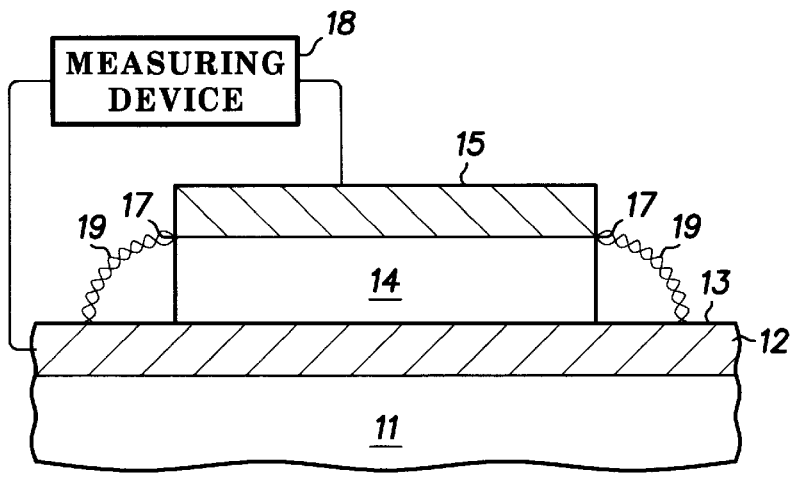
FIG. 1 is a simplified sectional view of an embodiment of an ultra-fine gap electrode structure according to the present invention.

Turning now to the drawings in which like reference characters indicate corresponding elements throughout the several views, attention is first directed to FIG. 1 which illustrates an ultra-fine gap electrode structure generally designated 10. Structure 10 includes an electrical contact 12 having a major surface 13. In this specific embodiment, electrical contact 12 is carried by a substrate 11. An insulating layer 14 is positioned overlying major surface 13 of electrical contact 12, and an electrical contact 15 is positioned overlying insulating layer 14. Electrical contact 15 includes an edge 17 spaced a molecular distance from major surface 13 of electrical contact 12. It should be noted that the thickness of insulating layer 14 determines the spacing between major surface 13 and edge 17.

Structure 10 is most conveniently fabricated in accordance with conventional semiconductor processes. Substrate 11 is provided, and electrical contact 12 is formed thereon such as by deposition of a metal. Metal-organic bondings are most conveniently carried out with, for example, gold and thiol, respectively. It is also contemplated that electrical contact 12 can be formed using heavily doped semiconductor material by implant or diffusion. Insulating layer 14 is formed on major surface 13 of electrical contact 12 by any conventional method such as deposition, growth or oxidation. Insulating layer 14 can be, for example, silicon oxide, silicon nitride, etc. By using conventional semiconductor techniques, the thickness of insulating layer 14 can be made very small, e.g. in the range of approximately 10 to 100 angstroms, and can be very accurately controlled. Electrical contact 15 is then formed overlying insulting layer 14. Electrical contact 15 can be formed in substantially the same manner as described above in conjunction with electrical contact 12.

By employing semiconductor processes, a plurality of structures 10 may be simultaneously fabricated with great uniformity. This is accomplished by blanket depositing or growing insulating layer 14 on contact 12. A plurality of contacts 15 can then be formed overlying insulating layer 14 and spaced from each other. The plurality of contacts 15 can be formed, for example, by depositing a blanket layer of metal, and using conventional mask and etch techniques to define individual contacts 15. Contacts 15 can subsequently be employed as masks to etch insulating layer 14 between individual contacts 15 to form a plurality of structures 10. Edge 17 of contact 15 is thus spaced a molecular distance, e.g. in a range of 10 Å to 100 Å, from major surface 13 of contact 15 with the spacing being accurately controlled.

Still referring to FIG. 1, structure 10 further includes a measuring device 18 electrically coupled to contacts 12 and 15. It should be noted that in some specific applications measuring device 18 can include semiconductor devices formed directly in or on substrate 11 adjacent to or in conjunction with one or more structures 10. A conductive organic molecule or ensemble of molecules 19, including a binding group at each end, is electrically connected between major surface 13 of electrical contact 12 and edge 17 of electrical contact 15. It will be understood that if metal contacts are employed as electrical contacts 12 and 15, each end of organic molecule or ensemble of molecules 19 will terminate in a metal binding group. Measuring device 18 is subsequently employed to measure the electrical characteristics of conductive organic molecule or ensemble of molecules 19.

The electrical characteristics to be measured include, for example, molecular conductivity. As described previously, the ends of the molecule or molecules bind to electrical contacts 12 and 15 forming bridges therebetween. By measuring the electrical characteristics of the bridge or bridges it will be possible to extract information about the electrical properties of the bridging molecules. This could be applied, for example, to study conductive molecules or detect the hybridization of DNA. Optical measurements have demonstrated high carrier mobilities in duplex DNA, but these properties have not yet been observed by direct electrical measurement. Structure 10 allows such a measurement. In use, single strand DNA bridging the gap between electrical contact 12 and 15 will have specific electrical properties. Hybridization can be detected by a change in the electrical characteristics brought on by duplex formation.

Figure 2:
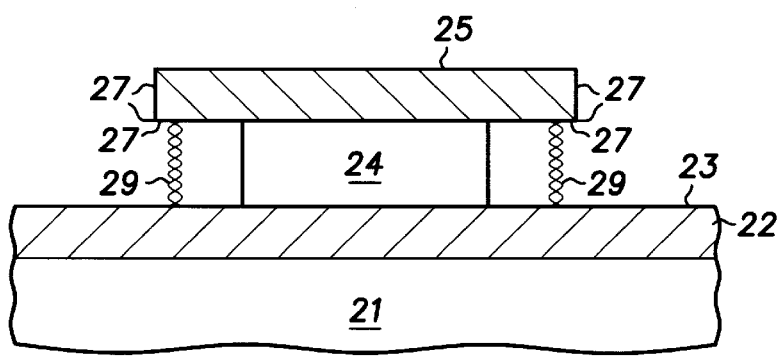
FIG. 2 is another embodiment of an ultra-fine gap electrode structure according to the present invention.

Turning now to FIG. 2, another embodiment of an ultra-fine gap electrode structure generally designated 20 is illustrated. Structure 20 includes an electrical contact 22 having a major surface 23. In this specific embodiment, electrical contact 22 is carried by a substrate 21. An insulating layer 24 is positioned overlying major surface 23 of electrical contact 22, and an electrical contact 25 is positioned overlying insulating layer 24. Electrical contact 25 includes an edge 27 spaced a molecular distance from major surface 23 of electrical contact 22. It should be noted that the thickness of insulating layer 24 determines the spacing between major surface 23 and edge 27. In this embodiment, insulating layer 24 can be undercut by etching using conventional semiconductor techniques. In this manner, edge 27 is expanded to extend inwardly, parallel to the opposing major surface 23. Edge 27 of contact 25, including the undercut area, is thus spaced a molecular distance, e.g. in a range of 10 Å to 100 Å, from major surface 23 of contact 25 with the spacing being accurately controlled. Thus, the molecular binding area (i.e. edge 27) is increased allowing a greater number of molecules or ensembles of molecules 29 to span the gap between electrical contacts 22 and 25.

Figure 3:
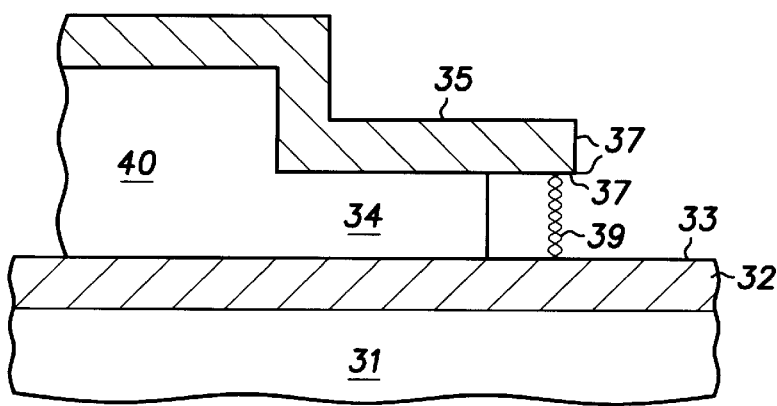
FIG. 3 is yet another embodiment of an ultra-fine gap electrode structure according to the present invention.

With reference to FIG. 3, yet another embodiment of an ultra-fine gap electrode structure generally designated 30 is illustrated. Structure 30 includes an electrical contact 32 having a major surface 33. In this specific embodiment, electrical contact 32 is carried by a substrate 31. An insulating layer 34 is positioned overlying major surface 33 of electrical contact 32, and an electrical contact 35 is positioned overlying insulating layer 34. Electrical contact 35 includes an edge 37 spaced a molecular distance from major surface 33 of electrical contact 32. It should be noted that the thickness of insulating layer 34 proximate edge 37 determines the spacing between major surface 33 and edge 37. In this embodiment, insulating layer 34 can be undercut or not as described in the previous embodiments. Thus, the molecular binding area (i.e. edge 77) is increased allowing a greater number of molecules or ensembles of molecules 39 to span the gap between electrical contacts 32 and 35.

Because insulating layer 34 is very thin, probing or electrically connecting a measuring device to structure 30 could cause shorting between electrical contacts 32 and 35. Shorting in this embodiment is avoided by forming insulating layer 34 with a thicker region such as a central mesa 40. Probing is then made to the portion of contact 35 overlying central mesa 40.

Thus, provided is a new and improved method of fabricating ultra-fine gap electrodes employing semiconductor processing techniques which method permits the fabrication of multiple ultra-fine gap electrode structures simultaneously and more readily and consistently.

While we have shown and described specific embodiments of the present invention, further modifications and improvements will occur to those skilled in the art. We desire it to be understood, therefore, that this invention is not limited to the particular forms shown and we intend in the appended claims to cover all modifications that do not depart from the spirit and scope of this invention.

What is claimed is:

1. A device for measuring electrical characteristics of a molecule comprising:
    a first electrical contact having a major surface;
    an insulating layer overlying the major surface of the first electrical contact;
    a second electrical contact overlying the insulating layer and having an edge spaced a molecular distance from the major surface of the first electrical contact; and
    at least one conductive organic molecule including a binding group at each end, electrically connected to the first electrical contact and the second electrical contact.

2. A device as claimed in claim 1 wherein the insulating layer is undercut from the edge of the second electrical contact.

3. A device as claimed in claim 1 wherein the insulating layer includes a thickened portion.

4. A device as claimed in claim 3 wherein the thickened portion includes a centrally located mesa.

5. A device as claimed in claim 1 wherein the molecular distance includes a range of approximately 10 to 100 angstroms.

6. A device as claimed in claim 1 further including a molecule or ensemble of molecules electrically connected between the first electrical contact and the second electrical contact.

7. A device as claimed in claim 6 wherein the molecule or ensemble of molecules include a binding group at each end.

8. A device as claimed in claim 7 wherein the molecule or ensemble of molecules include at least one conductive organic molecule.

9. A method for fabricating a device for measuring electrical characteristics of a molecule comprising the steps of:
    providing a first metal contact having a major surface;
    forming an insulating layer overlying the major surface of the first metal contact;

positioning a second metal contact overlying the insulating layer so as to have an edge spaced a molecular distance from the major surface of the first metal contact;

electrically connecting at least one conductive organic molecule including a binding group at each end, between the first metal contact and the second metal contact.

10. A method as claimed in claim 9 further including the step of undercutting the insulating layer from the edge of the second metal contact.

11. A method as claimed in claim 9 wherein the step of forming the insulating layer includes forming a thickened portion.

12. A method as claimed in claim 11 wherein the thickened portion includes a centrally located mesa.

13. A method as claimed in claim 9 wherein the steps of forming the insulating layer and positioning the second metal contact includes forming the insulating layer with a thickness in a range of approximately 10 to 100 angstroms and forming the second metal contact thereon.

14. A method as claimed in claim 9 further including the step of electrically connecting a molecule or ensemble of molecules between the first metal contact and the second metal contact.

15. A method as claimed in claim 14 wherein the molecule or ensemble of molecules include a metal binding group at each end.

16. A method as claimed in claim 15 wherein the molecule or ensemble of molecules include at least one conductive organic molecule.

17. A method of measuring electrical characteristics of a molecule comprising the steps of:

providing a first metal contact having a major surface;

forming an insulating layer overlying the major surface of the first metal contact;

positioning a second metal contact overlying the insulating layer so as to have an edge spaced a molecular distance from the major surface of the first metal contact;

electrically connecting a conductive organic molecule including a metal binding group at each end, between the first metal contact and the second metal contact;

connecting a measuring device between the first and second metal contacts characterized as measuring the electrical characteristics of the conductive organic molecule; and measuring the electrical characteristics of the conductive organic molecule.

18. A method as claimed in claim 17 wherein the steps of forming the insulating layer and positioning the second metal contact includes forming the insulating layer with a thickness in a range of approximately 10 to 100 angstroms and forming the second metal contact thereon.

* * * * *